United States Patent [19]

Theodoridis

[11] Patent Number: 5,310,723

[45] Date of Patent: May 10, 1994

[54] HERBICIDAL 3-(1-SUBSTITUTED-QUINOLIN-2-ON-7-YL)-1-SUBSTITUTED-6-TRIFLUOROMETHYLURACILS

[75] Inventor: George Theodoridis, Princeton, N.J.

[73] Assignee: FMC Corporation, Philadelphia, Pa.

[21] Appl. No.: 102,357

[22] Filed: Aug. 5, 1993

[51] Int. Cl.$^5$ .................. A01N 43/42; A01N 43/54; C07D 401/02
[52] U.S. Cl. .................. 504/243; 544/310
[58] Field of Search .................. 544/310; 504/243; A01N 43/54, 43/42

[56] References Cited

U.S. PATENT DOCUMENTS

| | | | |
|---|---|---|---|
| 3,235,357 | 2/1966 | Loux | 544/310 |
| 3,235,358 | 2/1966 | Soboczenski | 504/243 |
| 3,235,360 | 2/1966 | Soboczenski | 504/243 |
| 3,235,361 | 2/1966 | Loux | 504/243 |
| 3,235,363 | 2/1966 | Luckenbaugh et al. | 504/243 |
| 3,352,862 | 11/1967 | Loux | 504/243 |
| 3,352,863 | 11/1967 | Soboczenski | 504/243 |
| 3,360,521 | 12/1967 | Soboczenski | 504/310 |
| 3,360,522 | 12/1967 | Loux | 544/310 |
| 4,878,941 | 11/1989 | Theodoridis | 544/182 |
| 4,894,084 | 1/1990 | Theodoridis | 546/158 |
| 4,909,829 | 3/1990 | Theodoridis | 546/158 |

FOREIGN PATENT DOCUMENTS 61-165383 7/1986 Japan.
5-39272 2/1993 Japan.

Primary Examiner—Cecilia Tsang
Attorney, Agent, or Firm—H. Robinson Ertelt; Robert M. Kennedy

[57] ABSTRACT

Herbicidal compounds, compositions containing them, and a method for controlling weeds by application of the compositions is disclosed. The herbicidal compounds are 3-(1-substituted-quinolin-2-on-7-yl)-1-substituted-6-trifluoromethyluracils and related quinolinyl compounds of the formula

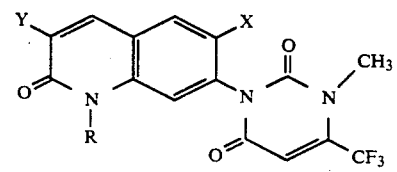

or

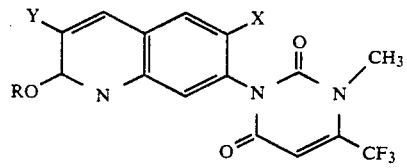

in which R is lower alkyl, lower alkenyl, lower alkynyl, lower haloalkyl, lower cyanoalkyl, lower alkoxy, lower alkoxy lower alkylene, and benzyl; X is hydrogen or halogen; and Y is hydrogen, lower alkyl, lower haloalkyl, halogen, lower alkoxy, lower haloalkoxy, lower alkylthio, lower alkoxy lower alkylene, lower alkylthio lower alkylene, and hydroxy.

17 Claims, No Drawings

HERBICIDAL 3-(1-SUBSTITUTED-QUINOLIN-2-ON-7-YL)-1-SUBSTITUTED-6-TRIFLUOROMETHYLURACILS

The invention described in this application pertains to weed control in agriculture, horticulture, and other fields where there is a desire to control unwanted plant growth. More specifically, the present application describes certain herbicidal 3-(1-substituted-quinolin-2-on-7-yl)-1-substituted-6-trifluoromethyluracils and related quinolinyl compounds, as well as compositions containing them, methods of preparing them, and methods for preventing or destroying undesired plant growth by preemergence or postemergence application of herbicidal compositions to the locus where control is desired. The herbicidal activity of the present compounds, which may be used to control a variety of both grassy and broadleaf plant species, has not previously been described.

Certain heterocyclic-substituted quinolinonyl, quinolinyl, and dihydroquinolinonyl compounds, in which the heterocycle is bonded to the 7-position of the quinoline ring, have previously been disclosed as herbicides. U.S. Pat. No. 4,878,941 discloses compounds in which a triazinedione is bonded to the quinoline ring; U.S. Pat. No. 4,894,084 discloses compounds in which a triazolinone is bonded to the quinoline ring; and U.S. Pat. No. 4,909,829 discloses compounds in which a tetrazolinone is bonded to the quinoline ring. In each of these patents, which were granted to the present applicant, the disclosed substitution pattern for the quinoline ring is similar to that of the present invention, and in each the preferred substitution pattern for the heterocycle appears highly specific to that heterocycle. Japanese Kokai No. 61-165383 discloses similar herbicidal compounds in which a tetrahydrophthalimide is bonded to the 7-position of the quinoline ring.

Japanese Kokai No. 5-39272 discloses a wide range of herbicidal compounds in which twenty-seven, optionally substituted, different heterocycles, including quinoline, may be bonded to a uracil, including trifluoromethyluracil, through a phenoxy bridge. Nothing in any reference of which applicant is aware suggests or makes obvious the high level of herbicidal activity found in the preferred compounds of the present invention.

It has now been found that 3-(1-substituted-quinolin-2-on-7-yl)-1-substituted-6-trifluoromethyluracils and related quinolinyl compounds are highly active herbicides. The novel compounds of the present invention are defined by the following generic structures:

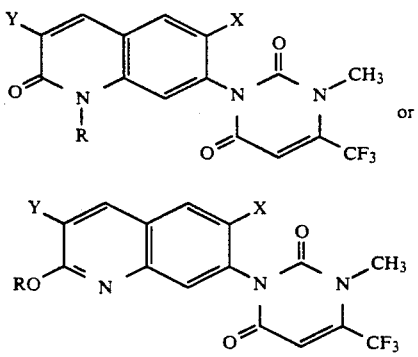

in which

R is lower alkyl, lower alkenyl, lower alkynyl, lower haloalkyl, lower cyanoalkyl, lower alkoxy, lower alkoxy lower alkylene, and benzyl;
X is hydrogen or halogen; and
Y is hydrogen, lower alkyl, lower haloalkyl, halogen, lower alkoxy, lower haloalkoxy, lower alkythio, lower alkoxy lower alkylene, lower alkylthio lower alkylene, and hydroxy.

Preferred are those compounds of the formula

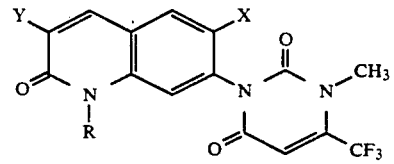

in which R is lower alkyl, lower alkenyl, lower alkynyl, lower haloalkyl, and lower cyanoalkyl; X is hydrogen or fluorine; and Y is hydrogen or lower alkyl.

Particularly preferred are those compounds in which R is ethyl, propyl, allyl, or propargyl; X is hydrogen or fluorine; and Y is hydrogen or methyl.

As used in this application "lower" means containing not more than six carbon atoms, preferably not more than three carbon atoms. "Halogen" means chlorine, fluorine, and bromine, preferably chlorine and fluorine.

The compounds of the present invention were prepared by methods known in the art. Ethyl 3-amino-4,4,4-trifluoro-2-butenoate was treated with sodium hydride in tetrahydrofuran and then reacted with an appropriately 2-substituted 4-nitrophenyl isocyanate, for example, 2-fluoro-4-nitrophenyl isocyanate, yielding the corresponding 3-(2-substituted-4-nitrophenyl)-6-trifluoromethyluracil. The uracil was then treated in-situ with potassium carbonate and reacted with methyl iodide, affording the corresponding 3-(2-substituted-4-nitrophenyl)-1-methyl-6-trifluoromethyluracil. The uracil, for example, 3-(2-fluoro-4-nitrophenyl)-1-methyl-6-trifluoromethyluracil, was reduced in the presence of iron powder and water in acetic acid, yielding the corresponding 3-(2-substituted-4-aminophenyl)-1-methyl-6-trifluoromethyluracil. The uracil was in turn treated with concentrated hydrochloric acid and sodium nitrite in water and acetone, which was then reacted with either a methyl 2-optionally substituted-propenoate or a 2-optionally substituted propenoic acid and copper(I) chloride, to yield the corresponding methyl 2-chloro-2-optionally substituted-3-[3-substituted-4-(1-methyl-6-trifluoromethyl-2,4(1H, 3H)-pyrimidinedion-3-yl)phenyl]propanoate or the 2-chloro-2-optionally substituted-3-[3-substituted-4-(1-methyl-6-trifluoromethyl-2,4(1H, 3H)-pyrimidinedion-3-yl)phenyl]-propanoic acid. The so-prepared acid or ester was then nitrated with 70% nitric acid in concentrated sulfuric acid and the cyclized in the presence of iron powder and water in acetic acid, to yield the corresponding 3-(3-chloro-3-optionally substituted 6-substituted-3,4-dihydroquinolin-2-on-7-yl)-1-methyl-6-trifluoromethyluracil. The quinoline derivative, for example, 3-(3-chloro-6-fluoro-3,4-dihydroquinolin-2-on-7-yl)-1-methyl-6-trifluoromethyluracil, was then dehydrohalogenated with triethylamine in tetrahydrofuran, affording the corresponding 3-(6-substituted-3-optionally substituted-quinolin-2-on-7-yl)-1-methyl-6-trifluoromethyluracil. The so-prepared (quinolin-2-on-7-yl)uracil was then treated with potassium carbonate in N,N- dimethylformamide and reacted with any one of a number of bromides, for example, 3-bromopropyne, to yield a mixture of N-substituted and O-substituted products, for example, 3-[1-(2-propyn-1-yl)-3-trifluoromethyl-6-fluoroquinolin-2-on-7-yl]-1-methyl-6-trifluoromethyluracil and 3-[2-(2-propyn-1-yloxy)-3-trifluoromethyl-6-fluoroquinolin-2-on-7yl]-1-methyl-6-trifluoromethyluracil. The N- and O-substituted products were readily separated by column chromatography.

EXAMPLE 1

Synthesis of 3-[1-(Propyn-2-Yl)-6-Fluoroquinolin-2-On-7-Yl]-1-Methyl-6-Trifluoromethyluracil (Compound 34)

Step A Synthesis of 2-fluoro-4-nitroaniline as an intermediate

A mixture of 10.0 grams (0.063 mole) of 3,4-difluoronitrobenzene and 40 mL of aqueous 29% ammonium hydroxide was placed in a pressure bottle and sealed. The mixture was stirred and heated at 135° C. for about 18 hours. The bottle and contents were then cooled and the bottle opened. A solid was collected by filtration and washed, first with water and then with petroleum ether. The solid was dried, yielding 9.4 grams of 2-fluoro-4-nitroaniline.

Step B Synthesis of 2-fluoro-4-nitrophenyl isocyanate as an intermediate

A solution of 9.4 grams (0.06 mole) of 2-fluoro-4-nitroaniline in 200 mL of toluene was stirred, and 5.9 grams (0.03 mole) of trichloromethyl chloroformate was added dropwise. Upon completion of addition, the reaction mixture was warmed to reflux, where it stirred for about 18 hours. After this time the reaction mixture was cooled and concentrated under reduced pressure, yielding about 10.9 grams of 2-fluoro-4-nitrophenyl isocyanate. The reaction product was used immediately in the next step.

Step C Synthesis of 3-(2-fluoro-4-nitrophenyl)-1-methyl-6-trifluoromethyluracil as an intermediate A stirred suspension of 2.7 grams (0.066 mole) of 60% sodium hydride (in mineral oil) in 125 mL of tetrahydrofuran was cooled to −20° C., and 11.0 grams (0.060 mole) of ethyl 3-amino-4,4,4-trifluoro-2-butenoate was added dropwise. Upon completion of addition, the reaction mixture was stirred for about 10 minutes, and 10.9 grams (0.060 mole) of 2-fluoro-4-nitrophenyl isocyanate was added dropwise. Upon completion of addition, the reaction mixture was allowed to warm to ambient temperature, where it was stirred for one hour. After this time the reaction mixture was warmed to reflux, where it was stirred for about 16 hours. The reaction mixture was then cooled to about ambient temperature, and 8.3 grams (0.060 mole) of potassium carbonate and 17.1 grams (0.120 mole) of methyl iodide were added. Upon completion of addition, the reaction mixture was warmed to reflux, where it was stirred for about 7 hours. The reaction mixture was cooled to ambient temperature and stirred with diethyl ether and water. The organic layer was separated, washed with water, and dried with magnesium sulfate. The mixture was filtered, and the filtrate was concentrated under reduced pressure to a residue. The residue was combined with a previous run (0.070 mole) of this reaction, and the mixture was subjected to column chromatography on silica gel. Elution was accomplished with heptane, 1:1 heptane-methylene chloride, and methylene chloride. The product-containing fractions were combined and concentrated under reduced pressure, yielding 17.7 grams of 3-(2-fluoro-4-nitrophenyl)-1-methyl-6-trifluoromethyluracil; mp 135°-136° C. The NMR spectrum was consistent with the proposed structure.

Step D Synthesis of 3-(4-amino-2-fluorophenyl)-1-methyl-6-trifluoromethyluracil as an intermediate A stirred suspension of 8.0 grams (0.024 mole) of 3-(2-fluoro-4-nitrophenyl)-1-methyl-6-trifluoromethyluracil in 200 mL of acetic acid was warmed to 50° C., at which time a solution was obtained. Water, 5 mL, was added to the reaction mixture, and then 8.0 grams (0.143 g-atom) of iron powder was added portion-wise during a 30 minute period. Upon completion of addition, the reaction mixture was allowed to cool to ambient temperature, where the product precipitated out. The reaction mixture was then warmed to 50° C., and the product went back into solution. The reaction mixture was stirred at 50° C. for one hour and then poured into water and ethyl acetate. The mixture was filtered through diatomaceous earth. The organic and aqueous layers in the filtrate were separated, and the aqueous layer was washed with ethyl acetate. The ethyl acetate wash was combined with the organic layer, and the combination was washed with water. The organic layer was dried with magnesium sulfate and filtered. The filtrate was concentrated under reduced pressure, yielding about 8 grams of product. The NMR spectrum of the product indicated that it was impure. The product was dissolved in methylene chloride, and the solution was washed with aqueous 5% sodium hydroxide. The organic layer was dried with magnesium sulfate and filtered. The filtrate was concentrated under reduced pressure, yielding 6.6 grams of product. The product was combined with that of a previous run (0.024 mole) of this reaction. The combination was subjected to column chromatography on silica gel, yielding 12.2 grams of 3-(4-amino-2-fluorophenyl)-1-methyl-6-trifluoromethyluracil. The NMR spectrum was consistent with the proposed structure.

Step E Synthesis of methyl 2-chloro-3-[3-fluoro-4-(1-methyl-6-trifluoromethyl-2,4(1H,3H)-pyrimidinedion-3-yl)phenyl]propanoate as an intermediate A stirred solution of 11.8 grams (0.039 mole) of 3-(4-amino-2-fluorophenyl)-1-methyl-6-trifluoromethyluracil and 25 mL of concentrated hydrochloric acid in 130 mL of acetone was cooled to below 10° C., and a solution of 2.7 grams (0.039 mole) of sodium nitrite in 10 mL of water was added dropwise. Upon completion of addition, the reaction mixture was stirred at below 10° C. for one hour. After this time 0.3 gram (0.003 mole) of copper(I) chloride was added in one portion. The reaction mixture was then cooled to 0° C., and 33.5 grams (0.390 mole) of methyl 2-propenoate was added slowly, portion-wise. The addition caused an exothermic reaction, which raised the reaction mixture temperature to about 15° C. Upon completion of addition, the reaction mixture was allowed to warm to ambient temperature, where it was stirred for about 16 hours. The reaction mixture was then poured into water, and the mixture was extracted with diethyl ether. The ether extract was dried with magnesium sulfate and filtered. The filtrate was concentrated under reduced pressure to a residue. The residue was subjected to column chromatography on silica gel. Elution was accomplished using 1:1 heptane-methylene chloride and methylene chloride. The product-containing fractions were combined and concentrated under reduced pressure, yielding 10.4 grams of methyl 2-chloro-3-[3-fluoro-4-(1-methyl-6-trifluoromethyl-2,4(1H,3H)-pyrimidinedion-3-yl)phenyl]-propanoate, mp 101°-103° C. The NMR spectrum was consistent with the proposed structure.

Step F Synthesis of methyl 2-chloro-3-[5-fluoro-2-nitro-4-(1-methyl-6-trifluoromethyl-2,4(1H,3H)-pyrimidinedion-3-yl)phenyl]propanoate as an intermediate A mixture of 10.4 grams (0.025 mole) of methyl 2-chloro-3-[3-fluoro-4-(1-methyl-6-trifluoromethyl-2,4(1H,3H)-pyrimidinedion-3-yl)phenyl]propanoate in 100 mL of concentrated sulfuric acid was stirred for two hours until the methyl propanoate was completely dissolved. The mixture was then cooled to 10° C., and 2.7 grams (0.030 mole) of 70% nitric acid was added dropwise while the temperature of the reaction mixture was held at 10° C. Upon completion of addition, the reaction mixture was allowed to warm to ambient temperature, where it was stirred for one hour. The reaction mixture was then poured into ice-water and stirred until the ice melted. The mixture was extracted with diethyl ether. The extract was washed with water and dried with magnesium sulfate. The mixture was filtered, and the filtrate was concentrated under reduced pressure to a residue. The residue was subjected to column chromatography on silica gel. Elution was accomplished using methylene chloride. The product-containing fractions were combined and concentrated under reduced pressure, yielding 3.2 grams of methyl 2-chloro-3-[5-fluoro-2-nitro-4-(1-methyl-6-trifluoromethyl-2,4(1H,3H)-pyrimidinedion-3-yl)phenyl]propanoate, mp 60°-65° C. The NMR spectrum was consistent with the proposed structure.

Step G Synthesis of 3-(3-chloro-6-fluoro-3,4-dihydroquinolin-2-on-7-yl)-1-methyl-6-trifluoromethyluracil as an intermediate This compound was prepared in a manner analogous to that of Step D of this Example, using 2.9 grams (0.006 mole) of methyl 2-chloro-3-[5-fluoro-2-nitro-4-(1-methyl-6-trifluoromethyl-2,4(1H,3H)-pyrimidinedion-3-yl)phenyl]propanoate, 2.0 grams (0.036 g-atom) of iron powder, and 5 mL of water in 50 mL of acetic acid. The product from this reaction was combined with that from another run (0.014 mole) of this reaction. The combination was subjected to column chromatography on silica gel. Elution was accomplished using heptane, 1:1 heptane-ethyl acetate, and ethyl acetate. The product-containing fractions were combined and concentrated under reduced pressure, yielding 5.2 grams of 3-(3-chloro-6-fluoro-3,4-dihydroquinolin-2-on-7-yl)-1-methyl-6-trifluoromethyluracil. The NMR spectrum was consistent with the proposed structure.

Step H Synthesis of 3-(6-fluoroquinolin-2-on-7-yl)-1-methyl-6-trifluoromethyluracil as an intermediate A stirred solution of 5.2 grams (0.013 mole) of 3-(3-chloro-6-fluoro-3,4-dihydroquinolin-2-on-7-yl)-1-methyl-6-trifluoromethyluracil and 6.2 grams (0.061 mole) of triethylamine in 200 mL of tetrahydrofuran was concentrated under reduced pressure to a residue. The residue was dissolved in methylene chloride and washed with water. The organic layer was dried with magnesium sulfate and filtered. The filtrate was concentrated under reduced pressure, yielding 4.5 grams of 3-(6-fluoroquinolin-2-on-7-yl)-1-methyl-6-trifluoromethyluracil, mp 179° C., dec. The NMR spectrum was consistent with the proposed structure.

Step I Synthesis of 3-[1-(2-propyn-1-yl)-6-fluoroquinolin-2-on-7-yl]-1-methyl-6-trifluoromethyluracil (Compound 34)

A stirred solution of 0.6 gram (0.002 mole) of 3-(6-fluoroquinolin-2-on-7-yl)-1-methyl-6-trifluoromethyluracil, 0.5 gram (0.003 mole) of 3-bromopropyne, and 0.5 gram (0.003 mole) of potassium carbonate in 40 mL of N,N-dimethylformamide was stirred at ambient temperature for about 16 hours. The reaction mixture was then subjected to column chromatography on silica gel. Elution was accomplished using 1:1 ethyl acetate-heptane and ethyl acetate. The product-containing fractions were combined and concentrated under reduced pressure, yielding 0.4 gram of 3-[1-(2-propyn-1-yl)-6-fluoroquinolin-2-on-7-yl]-1-methyl-6-trifluoromethyluracil, mp 236°-238° C. The NMR spectrum was consistent with the proposed structure. Other fractions were combined and concentrated under reduced pressure, yielding a small amount of the O-alkylated product, 3-[2-(2-propyn-1-yloxy)-6-fluoroquinolin-2-on-7-yl]-1-methyl-6-trifluoromethyluracil.

EXAMPLE 2

Synthesis of
3-[1-(2-Propen-1-Yl)-6-Fluoroquinolin-2-On-7-Yl]-1-Methyl-6-Trifluoromethyluracil (Compound 26) and
3-[2-(2-Propen-1-Yloxy)-6-Fluoroquinolin-2-On-7-Yl]-1-Methyl-6-Trifluoromethyluracil (Compound 20A)

These compounds were prepared in a manner analogous to that of Step I of Example 1, using 0.5 gram (0.001 mole) of 3-(6-fluoroquinolin-2-on-7-yl)-1-methyl-6-trifluoromethyluracil (prepared in Step H of Example 1), 0.5 gram (0.003 mole) of 3-bromopropene, and 0.4 gram (0.003 mole) potassium carbonate in 40 mL of N,N-dimethylformamide. The crude reaction product was subjected to column chromatography on silica gel. Elution was accomplished using 1:1 ethyl acetate-heptane and ethyl acetate. The appropriate, product-containing fractions were combined and concentrated under reduced pressure, yielding 0.3 gram of 3-[1-(2-propen-1-yl)-6-fluoroquinolin-2-on-7-yl]-1-methyl-6-trifluoromethyluracil (Compound 26), mp 178°-179° C. Other product-containing fractions were combined and concentrated under reduced pressure, yielding 0.2 gram of the O-alkylated product, 3-[2-(2-propen-1-yloxy)-6-fluoroquinolin-2-on-7-yl]-1-methyl-6-trifluoromethyluracil (Compound 20A). The NMR spectra were consistent with the proposed structures.

EXAMPLE 3

Synthesis of
3-[1-(2-Propyn-1-Yl)-3-Trifluoromethyl-6-Fluoroquinolin-2-On-7-Yl]-1-Methyl-6-Trifluoromethyluracil (Compound 42) and
3-[2-(2-Propyn-1-Yloxy)-3-Trifluoromethyl-6-Fluoroquinolin-2-On-7-Yl]-1-Methyl-6-Trifluoromethyluracil (Compound 26A)

Step A Synthesis of 2-chloro-2-trifluoromethyl-3-[3-fluoro-4-(1-methyl-6-trifluoromethyl-2,4(1H,3H)-pyrimidinedion-3-yl)phenyl]propanoic acid as an intermediate This compound was prepared in a manner analogous to that of Step E of Example 1, using 6.0 grams (0.020 mole) of 3-(4-amino-2-fluorophenyl)-1-methyl-6-trifluoromethyluracil (prepared as in Step D of Example 1), 28.0 grams (0.200 mole) of 2-trifluoromethylpropenoic acid, 1.4 grams (0.020 mole) of sodium nitrite, 0.5 gram (0.005 mole) of copper(I) chloride, and 30 mL of concentrated hydrochloric acid in 150 mL of acetone, yielding 5.8 grams of 2-chloro-2-trifluoromethyl-3-[3-fluoro-4-(1-methyl-6-trifluoromethyl-2,4(1H,3H)-pyrimidinedion-3-yl)phenyl]propanoic acid. The NMR spectrum was consistent with the proposed structure. This reaction differed from Step E of Example 1 in that the intermediate propene used here was the acid, rather than the methyl ester, as was used in Step E of Example 1.

Step B Synthesis of 2-chloro-2-trifluoromethyl-3-[5-fluoro-2-nitro-4-(1-methyl-6-trifluoromethyl-2,4(1H,3H)-pyrimidinedion-3-yl)phenyl]propanoic acid as an intermediate This compound was prepared in a manner analogous to that of Step F of Example 1, using 7.7 grams (0.016 mole) of 2-chloro-2-trifluoromethyl-3-[3-fluoro-4-(1-methyl-6-trifluoromethyl-2,4(1H,3H)-pyrimidinedion-3-yl)phenyl]propanoic acid. and 1.7 grams (0.019 mole) of 70% nitric acid in 100 mL of concentrated sulfuric acid, yielding 7.3 grams of 2-chloro-2-trifluoromethyl-3-[5-fluoro-2-nitro-4-(1-methyl-6-trifluoromethyl-2,4(1H,3H)-pyrimidinedion-3-yl)phenyl]propanoic acid. The NMR spectrum was consistent with the proposed structure.

Step C Synthesis of 3-(3-chloro-6-fluoro-3,4-dihydro-3-trifluoromethylquinolin-2-on-7-yl)-1-methyl-6-trifluoromethyluracil as an intermediate This compound was prepared in a manner analogous to that of Step D of Example 1, using 6.8 grams (0.013 mole) of 2-chloro-2-trifluoromethyl-3-[5-fluoro-2-nitro-4-(1-methyl-6-trifluoromethyl-2,4(1H,3H)-pyrimidinedion-3-yl)phenyl]propanoic acid, 7.0 grams (0.130 g-atom) of iron powder, and 20 mL of water in 100 mL of acetic acid, yielding 3.2 grams of 3-(3-chloro-6-fluoro-3,4-dihydro-3-trifluoromethylquinolin-2-on-7-yl)-1-methyl-6-trifluoromethyluracil. The NMR spectrum was consistent with the proposed structure.

Step D Synthesis of 3-(6-fluoro-3-trifluoromethylquinolin-2-on-7-yl)-1-methyl-6-trifluoromethyluracil as an intermediate This compound was prepared in a manner analogous to that of Step H of Example 1, using 3.2 grams (0.007 mole) of 3-(3-chloro-6-fluoro-3,4-dihydro-3-trifluoromethylquinolin-2-on-7-yl)-1-methyl -6-trifluoromethyluracil and 3.2 grams (0.031 mole) of triethylamine in 100 mL of tetrahydrofuran. The product was recrystallized from ethanol, yielding 1.4 grams of 3-(6-fluoro-3-trifluoromethylquinolin-2-on-7-yl)-1-methyl-6-trifluoromethyluracil. The NMR spectrum was consistent with the proposed structure.

Step E Synthesis of 3-[1-(2-propyn-1-yl)-3-trifluoromethyl-6-fluoroquinolin-2-on-7-yl]-1-methyl-6-trifluoromethyluracil (Compound 42) and 3-[2-(2-propyn-1-yloxy)-3-trifluoromethyl-6-fluoroquinolin-2-on-7yl]-1-methyl-6-trifluoromethyluracil (Compound 26A)

These compounds were prepared in a manner analogous to that of Step I of Example 1, using 1.0 gram (0.002 mole) of 3-(6-fluoro-3-trifluoromethylquinolin-2-on-7-yl)-1-methyl-6-trifluoromethyluracil, 0.7 gram (0.005 mole) of 80% 3-bromopropyne, and 0.7 gram (0.005 mole) of potassium carbonate in 40 mL of N,N-dimethylformamide. The crude reaction product was subjected to column chromatography on silica gel. Elution was accomplished using 1:4 ethyl acetate-hexane and 1:1 ethyl acetatehexane. The appropriate product-containing fractions were combined and concentrated under reduced pressure, yielding 0.8 gram of 3-[1-(2-propyn-1-yl)-3-trifluoromethyl-6-fluoroquinolin-2-on-7-yl]-1-methyl-6-trifluoromethyluracil (Compound 42), mp 248°-250° C. Other product-containing fractions were combined and concentrated under reduced pressure, yielding 0.1 gram of the O-alkylated product, 3-[2-(2-propyn-1-yloxy)-3-trifluoromethyl-6-fluoroquinolin-2-on-7-yl]-1-methyl-6-trifluoromethyluracil (Compound 26A). The NMR spectra were consistent with the proposed structures.

Representative compounds of the invention prepared by the methods exemplified above are shown in Tables 1 and 1A.

HERBICIDAL ACTIVITY

The herbicides of this invention were tested for pre- and post-emergence herbicidal activity against a variety of crops and weeds. The test plants included soybean (*Glycine max* var. Williams), field corn (*Zea mays* var. Agway 425X), wheat (*Triticum aestivum* var. Wheaton), morningglory (*Ipomoea lacunosa* or *Ipomoea hederacea*), velvetleaf (*Abutilon theophrasti*), green foxtail (*Setaria viridis*), Johnsongrass (*Sorghum halepense*), blackgrass (*Aloepecurus myosuroides*), common chickweed (*Stellaria media*), and common cocklebur (*Xanthium pensylvanicum*).

For preemergence testing, two disposable fiber flats (8 cm×15 cm×25 cm) for each rate of application of each candidate herbicide were filled to an approximate depth of 6.5 cm with steam-sterilized sandy loam soil. The soil was leveled and impressed with a template to provide five evenly spaced furrows 13 cm long and 0.5 cm deep in each flat. Seeds of soybean, wheat, corn, green foxtail, and Johnsongrass were planted in the furrows of the first flat, and seeds of velvetleaf, morningglory, common chickweed, cocklebur, and blackgrass were planted in the furrows of the second flat. The five-row template was employed to press the seeds firmly into place. A topping soil of equal portions of sand and sandy loam soil was placed uniformly on top of each flat to a depth of approximately 0.5 cm. Flats for postemergence testing were prepared in the same manner except that they were planted 8–12 days prior to the preemergence flats and were placed in a greenhouse and watered, thus allowing the seeds to germinate and the foliage to develop.

In both pre- and postemergence tests, a stock solution of the candidate herbicide was prepared by dissolving a predetermined weight of the compound in 20 mL of water/acetone (50/50) containing 0.5% v/v sorbitan monolaurate. Thus for an application rate of up to 3000 g/ha of herbicide, 0.27 g of candidate herbicide was dissolved in 20 mL of the aqueous acetone to prepare the stock solution. A portion (10 mL) was then diluted with water acetone (50/50) to 45 mL, the volume required to correspond to a spray volume of 1000 L/ha. The remaining stock solution was then used to prepare lower application rates.

For the nominal 0.1 kg/ha rate reported in Tables 2 and 3, 0.3 mL of stock solution was diluted with 45 mL of water/acetone (50/50) to 45.3 mL. (This dilution actually results in a rate of 0.09 kg/ha, but is reported as 0.1.)

The preemergence flats were initially subjected to a light water spray. The four flats were placed two by two along a conveyor belt (i.e., the two preemergence followed by the two postemergence flats). The conveyor belt fed under a spray nozzle mounted about ten inches above the postemergent foliage. The preemergent flats were elevated on the belt so that the soil surface was at the same level below the spray nozzle as the foliage canopy of the postemergent plants. The spray of herbicidal solution was commenced and once stabilized, the flats were passed under the spray at a speed to receive a coverage equivalent of 1000 L/ha. The pre-emergence flats were watered immediately thereafter, placed in the greenhouse and watered regularly at the soil surface. The postemergence flats were immediately placed in the green-house and not watered until 24 hours after treatment with the test solution. Thereafter they were regularly watered at ground level. After 17-21 days the plants were examined and the phytotoxicity data were recorded.

Herbicidal activity data at selected application rates are given for various compounds of this invention in Table 2 and Table 3. The test compounds are identified by numbers which correspond to those in Table 1.

Phytotoxicity data were taken as percent control. Percent control was determined by a method similar to the 0 to 100 rating system disclosed in "Research Methods in Weed Science," 2nd ed., B. Truelove, Ed.; Southern Weed Science Society; Auburn University, Auburn, Ala., 1977. The rating system is as follows:

| Rating Percent Control | Herbicide Rating System | | |
|---|---|---|---|
| | Description of Main Categories | Crop Description | Weed Description |
| 0 | No effect | No crop reduction or injury | No weed control |
| 10 | | Slight discoloration or stunting | Very poor weed control |
| 20 | Slight effect | Some discoloration, stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery doubtful | Deficient to moderate weed control |
| 60 | | Lasting crop injury, no recovery | Moderate weed control |
| 70 | | Heavy injury and stand loss | Control somewhat less than satisfactory |
| 80 | Severe | Crop nearly destroyed, a few survivors | Satisfactory to good weed control |
| 90 | | Only occasional live plants left | Very good to excellent control |
| 100 | Complete effect | Complete crop destruction | Complete weed destruction |

For herbicidal application the active compounds of the invention are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and post-emergence herbicides, are in the form of finely divided particles which disperse readily in water or other dispersant. A wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Frequently additional wetting agent(s) and/or oil will be added to the tank mix for postemergence application to facilitate dispersion on the foliage and absorption by the plant.

Other useful formulations for herbicidal applications are emulsifiable concentrates (ECs), which are homogeneous liquid compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing, or emulsifying agents used in agricultural formulations include, but are not limited to, the alkyl and alkylaryl sulfonates and the sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent(s), when used, normally comprises from 1 to 15% by weight of the composition.

Other useful formulations include suspensions of the active ingredient in a relatively non-volatile liquid such as water, corn oil, kerosene, propylene glycol, or other suitable liquid carrier.

Still other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as carbon dioxide, propane, or butane, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful with the present herbicidal compounds. For use by the farmer on the field, the granular formulations, emulsifiable concentrates, flowable concentrates, solutions, etc., may be diluted with water to give a concentration of active ingredient in the range of, say, 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is, of course, employed; the amount may be as low as, e.g., about 10 to 100 g/ha, preferably about 30 to 60 g/ha. For field use, where there are losses of herbicide, higher application rates (e.g., four times the greenhouse testing rates mentioned above) may be employed.

The active herbicidal compounds of this invention may be used in combination with other herbicides, e.g., they may be mixed with, say, a lesser, equal, or larger amount of a known herbicide such as aryloxyalkanoic acid herbicides such as (2,4-dichlorophenoxy)acetic acid (2,4-D), (4-chloro-2-methylphenoxy)acetic acid (MCPA), (+/−)-2-(4-chloro-2-methylphenoxy)-propanoic acid (MCPP); urea herbicides, such as N,N-dimethyl-N'-[4-(1-methylethyl)phenyl]urea (isoproturon); imidazolinone herbicides, such as 2-[4,5-dihydro-4-methyl-4-(1-methylethyl)-5-oxo-1H-imidazol-2-yl]-3-pyridinecarboxylic acid (imazapyr), a reaction product comprising (+/−)-2-[4,5-dihydro-4-methyl-4-(1-methylethyl)-5-oxo-1H-imidazol-2-yl]-4-methylbenzoic acid and (+/−)-2-[4,5-dihydro-4-methyl-4-(1-methylethyl)-5-oxo-1H-imidazol-2-yl]-5-methylbenzoic acid (imazamethabenz), (+/−)-2-[4,5-dihydro-4-methyl-4-(1-methylethyl)-5-oxo-1H-imidazol-2-yl]-5-ethyl-3-pyridinecarboxylic acid (imazethapyr), and (+/−)-2-[4,5-dihydro-4-methyl-4-(1-methylethyl)-5-oxo-1H-imidazol-2-yl]-3-quinolinecarboxylic acid (imazaquin); diphenyl ether herbicides, such as 5-[2-chloro-4-(trifluoromethyl)phenoxy]-2-nitrobenzoic acid (acifluorfen), methyl 5-(2,4-dichlorophenoxy)-2-nitrobenzoate (bifenox), and 5-[2-chloro-4-(trifluoromethyl)phenoxy]-N-(methylsulfonyl)-2-nitrobenzamide (fomasafen); hydroxybenzonitrile herbicides, such as 4-hydroxy-3,5-diiodobenzonitrile (ioxynil), and 3,5-dibromo-4-hydroxybenzonitrile (bromoxynil); sulfonylurea herbicides, such as 2-[[[[(4-chloro-6-methoxy-2-pyrimidinyl)amino]carbonyl]amino]sulfonyl]benzoic acid (chlorimuron), 2-chloro-N-[[(4-methoxy-6-methyl-1,3,5-triazin-2-yl)amino]carbonyl]benzenesulfonamide (chlorsulfuron), 2-[[[[(4,6-dimethoxy-2-pyrimidinyl)amino]carbonyl]amino]sulfonyl]methyl]benzoic acid (bensulfuron), 2-[[[[(4,6-dimethoxy-2-pyrimidinyl)amino]carbonyl]amino]sulfonyl]-1-methyl-1H-pyrazol-4-carboxylic acid (pyrazosulfuron), 3-[[[[(4-methoxy-6-methyl-1,3,5-triazin-2-yl)amino]carbonyl]amino]sulfonyl]-2-thiophenecarboxylic acid (thifensulfuron), and 2-(2-chloroethoxy)-N-[[(4-methoxy-6-methyl-1,3,5-triazin-2-yl)amino]carbonyl]benzenesulfonamide (triasulfuron); 2-(4-aryloxyphenoxy)alkanoic acid herbicides, such as (+/−)-2-[4-[(6-chloro-2-benzoxazolyl)oxy]-phenoxy]propanoic acid (fenoxaprop), (+/−)-2-[4-[[5-(trifluoromethyl)-2-pyridinyl]oxy]phenoxy]propanoic acid (fluazifop), (+/−)-2-[4-(6-chloro-2-quinoxalinyl)oxy]phenoxy]propanoic acid (quizalofop), and (+/−)-2-[-(2,4-dichlorophenoxy)phenoxy]propanoic acid (diclofop); benzothiadiazinone herbicides, such as 3-(1-methylethyl)-1H-2,1,3-benzothiadiazin-4(3H)-one 2,2-dioxide (bentazone); 2-chloroacetanilide herbicides, such as N-(butoxymethyl)-2-chloro-2',6'-diethylacetanilide (butachlor); arenecarboxylic acid herbicides, such as 3,6-dichloro-2-methoxybenzoic acid (dicamba); and pyridyloxyacetic acid herbicides, such as [(4-amino-3,5-dichloro-6-fluoro-2-pyridinyl)oxy]acetic acid (fluroxypyr).

It is apparent that various modifications may be made in the formulation and application of the compounds of this invention without departing from the inventive concepts herein as defined in the claims.

TABLE 1

Herbicidal 3-(1-substituted-quinolin-2-on-7-yl)-1-substituted-6-trifluoromethyluracils

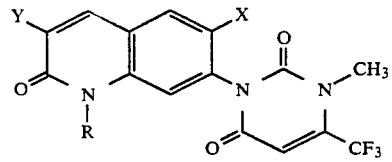

| Cmpd. No. | X | Y | R |
|---|---|---|---|
| 1 | H | H | —CH₃ |
| 2 | F | H | —CH₃ |
| 3 | F | —CH₃ | —CH₃ |
| 4 | H | H | —C₂H₅ |
| 5 | Cl | H | —C₂H₅ |
| 6 | Cl | —CH₃ | —C₂H₅ |
| 7 | F | H | —C₂H₅ |
| 8 | F | —CH₃ | —C₂H₅ |
| 9 | H | H | n-C₃H₇ |
| 10 | Cl | H | n-C₃H₇ |
| 11 | Cl | —CH₃ | n-C₃H₇ |
| 12 | F | H | n-C₃H₇ |
| 13 | F | —CH₃ | n-C₃H₇ |
| 14 | F | —CO₂CH₃ | n-C₃H₇ |
| 15 | F | H | n-C₄H₉ |
| 16 | F | H | —CH₂CH₂F |

TABLE 1-continued
Herbicidal 3-(1-substituted-quinolin-2-on-7-yl)-1-substituted-6-trifluoromethyluracils

| Cmpd. No. | X | Y | R |
|---|---|---|---|
| 17 | F | H | —OCH₃ |
| 18 | F | H | —CH₂OCH₃ |
| 19 | F | H | —CH₂CH₂OCH₃ |
| 20 | Cl | H | —CH₂CH₂CH₂F |
| 21 | Cl | —CH₃ | —CH₂CH₂CH₂F |
| 22 | F | H | —H₂C-phenyl |
| 23 | H | H | —CH₂C=CH₂ |
| 24 | Cl | H | —CH₂C=CH₂ |
| 25 | Cl | —CH₃ | —CH₂C=CH₂ |
| 26 | F | H | —CH₂C=CH₂ |
| 27 | F | —CH₃ | —CH₂C=CH₂ |
| 28 | F | —CF₃ | —CH₂C=CH₂ |
| 29 | F | —CO₂CH₃ | —CH₂C=CH₂ |
| 30 | H | H | —CH₂C≡CH |
| 31 | Cl | H | —CH₂C≡CH |
| 32 | Cl | —CH₃ | —CH₂C≡CH |
| 33 | Br | H | —CH₂C≡CH |
| 34 | F | H | —CH₂C≡CH |
| 35 | F | Cl | —CH₂C≡CH |
| 36 | F | Br | —CH₂C≡CH |
| 37 | F | F | —CH₂C≡CH |
| 38 | F | —CH₃ | —CH₂C≡CH |
| 39 | F | —C₂H₅ | —CH₂C≡CH |
| 40 | F | —CH(CH₃)₂ | —CH₂C≡CH |
| 41 | F | —CHF₂ | —CH₂C≡CH |
| 42 | F | —CF₃ | —CH₂C≡CH |
| 43 | F | —OCH₃ | —CH₂C≡CH |
| 44 | F | —OCHF₂ | —CH₂C≡CH |
| 45 | F | —SCH₃ | —CH₂C≡CH |
| 46 | F | —CH₂SCH₃ | —CH₂C≡CH |
| 47 | F | —OH | —CH₂C≡CH |
| 48 | F | —CO₂CH₃ | —CH₂C≡CH |
| 49 | F | H | —CH₂C≡N |
| 50 | F | H | —CH₂CO₂CH₃ |
| 51 | F | H | —CH₂CO₂C₂H₅ |

TABLE 1A
Herbicidal 3-(2-substituted-quinolin-7-yl)-1-substituted-6-trifluoromethyluracils

| Cmpd. No. | X | Y | R |
|---|---|---|---|
| 1A | H | H | —C₂H₅ |
| 2A | Cl | H | —C₂H₅ |
| 3A | Cl | —CH₃ | —C₂H₅ |
| 4A | F | —CH₃ | —CH₃ |
| 5A | F | H | —C₂H₅ |
| 6A | F | —CH₃ | —C₂H₅ |
| 7A | H | H | n-C₃H₇ |
| 8A | Cl | H | n-C₃H₇ |
| 9A | Cl | —CH₃ | n-C₃H₇ |
| 10A | F | H | n-C₃H₇ |
| 11A | F | —CH₃ | n-C₃H₇ |
| 12A | F | —CO₂CH₃ | n-C₃H₇ |

TABLE 1A-continued
Herbicidal 3-(2-substituted-quinolin-7-yl)-1-substituted-6-trifluoromethyluracils

| Cmpd. No. | X | Y | R |
|---|---|---|---|
| 13A | F | H | —CH(CH₃)₂ |
| 14A | Cl | H | —CH₂CH₂CH₂F |
| 15A | Cl | —CH₃ | —CH₂CH₂CH₂F |
| 16A | F | H | —H₂C-phenyl |
| 17A | H | H | —CH₂C=CH₂ |
| 18A | Cl | H | —CH₂C=CH₂ |
| 19A | Cl | —CH₃ | —CH₂C=CH₂ |
| 20A | F | H | —CH₂C=CH₂ |
| 21A | F | —CH₃ | —CH₂C=CH₂ |
| 22A | F | —CF₃ | —CH₂C=CH₂ |
| 23A | F | —CO₂CH₃ | —CH₂C=CH₂ |
| 24A | Cl | H | —CH₂C≡CH |
| 25A | F | —CH₃ | —CH₂C≡CH |
| 26A | F | —CF₃ | —CH₂C≡CH |
| 27A | F | —CO₂CH₃ | —CH₂C≡CH |
| 28A | F | H | —CH₂CO₂CH₃ |
| 29A | F | H | —CH₂CO₂C₂H₅ |

TABLE 2
PREEMERGENCE HERBICIDAL ACTIVITY (% CONTROL)

| Cmpd. No. | 1 | 2 | 3 | 4 | 5 | 6 | 7 | 8 |
|---|---|---|---|---|---|---|---|---|
| Rate (kg/ha) | 0.1 | 0.1 | 0.1 | 0.1 | 0.1 | 0.1 | 0.1 | 0.1 |
| Species | | | | | | | | |
| Soybean | 85 | 100 | 95 | 100 | 70 | 50 | 100 | 100 |
| Wheat | 80 | 80 | 50 | 95 | 20 | 20 | 100 | 100 |
| Corn | 85 | 90 | 100 | 90 | 40 | 80 | 100 | 100 |
| Velvetleaf | 100 | 100 | 100 | 100 | 100 | 100 | 100 | 100 |
| Morningglory | 100 | 100 | 100 | 100 | 70 | 60 | 100 | 100 |
| Chickweed | 100 | 100 | 100 | 100 | 20 | 0 | 100 | ND |
| Cocklebur | 80 | 100 | 80 | 100 | 20 | 10 | 100 | 100 |
| Blackgrass | 90 | 90 | 60 | 100 | 30 | 20 | 100 | 100 |
| Green foxtail | 100 | 100 | 100 | 100 | 85 | 90 | 100 | 100 |
| Johnsongrass | 90 | 100 | 100 | 100 | 85 | 70 | 100 | 100 |

| Cmpd. No. | 9 | 10 | 11 | 12 | 13 | 14 | 20 | 21 |
|---|---|---|---|---|---|---|---|---|
| Rate (kg/ha) | 0.1 | 0.1 | 0.1 | 0.1 | 0.1 | 0.1 | 0.1 | 0.1 |
| Species | | | | | | | | |
| Soybean | 100 | 70 | 30 | 100 | 100 | 0 | 50 | 90 |
| Wheat | 95 | 70 | 20 | 90 | 95 | 0 | 10 | 20 |
| Corn | 95 | 90 | 90 | 95 | 95 | 0 | 60 | 70 |
| Velvetleaf | 100 | 100 | 100 | 100 | 100 | 0 | 100 | 95 |
| Morningglory | 100 | 80 | 70 | 100 | 100 | 0 | 30 | 30 |
| Chickweed | 100 | 0 | 0 | ND | 100 | 10 | 30 | 0 |
| Cocklebur | 95 | 30 | 20 | 90 | 100 | 0 | 10 | 0 |
| Blackgrass | 100 | 80 | 40 | 90 | 100 | 0 | 30 | 10 |
| Green foxtail | 100 | 100 | 95 | 100 | 100 | 0 | 90 | 80 |
| Johnsongrass | 100 | 95 | 85 | 100 | 100 | 0 | 85 | 70 |

| Cmpd. No. | 22 | 23 | 24 | 25 | 26 | 27 | 28 | 29 |
|---|---|---|---|---|---|---|---|---|
| Rate (kg/ha) | 0.1 | 0.1 | 0.1 | 0.1 | 0.1 | 0.1 | 0.1 | 0.1 |
| Species | | | | | | | | |
| Soybean | 100 | 100 | 90 | 50 | 100 | 100 | 30 | 0 |
| Wheat | 70 | 100 | 70 | 40 | 100 | 95 | 0 | 0 |
| Corn | 85 | 90 | 85 | 90 | 100 | 95 | 60 | 0 |
| Velvetleaf | 100 | 100 | 100 | 100 | 100 | 100 | 95 | 0 |
| Morningglory | 90 | 100 | 95 | 95 | 100 | 100 | 10 | 0 |
| Chickweed | 100 | 100 | 20 | 60 | 100 | 100 | 95 | 0 |
| Cocklebur | 80 | 100 | 90 | 20 | 100 | 100 | 20 | 0 |
| Blackgrass | 80 | 100 | 80 | 70 | 100 | 100 | 40 | 0 |

TABLE 2-continued
PREEMERGENCE HERBICIDAL ACTIVITY (% CONTROL)

| Green foxtail | 100 | 100 | 100 | 100 | 100 | 100 | 20 | 0 |
|---|---|---|---|---|---|---|---|---|
| Johnsongrass | 95 | 100 | 95 | 90 | 100 | 100 | 50 | 10 |

| Cmpd. No. | 30 | 31 | 32 | 34 | 38 | 42 | 48 | 49 |
|---|---|---|---|---|---|---|---|---|
| Rate (kg/ha) | 0.1 | 0.1 | 0.1 | 0.1 | 0.1 | 0.1 | 0.1 | 0.1 |
| Species | | | | | | | | |
| Soybean | 100 | 100 | 90 | 100 | 100 | 100 | 0 | 100 |
| Wheat | 100 | 80 | 30 | 100 | 100 | 40 | 0 | 60 |
| Corn | 95 | 90 | 95 | 100 | 95 | 100 | 10 | 95 |
| Velvetleaf | 100 | 100 | 100 | 100 | 100 | 100 | 0 | 100 |
| Morningglory | 100 | 100 | 90 | 100 | 100 | 95 | 0 | 100 |
| Chickweed | 100 | 100 | 100 | 100 | 100 | 100 | 20 | ND |
| Cocklebur | 100 | 100 | 70 | 100 | 100 | 90 | 0 | 100 |
| Blackgrass | 100 | 90 | 90 | 100 | 100 | 70 | 0 | 100 |
| Green foxtail | 100 | 100 | 100 | 100 | 100 | 100 | 10 | 100 |
| Johnsongrass | 100 | 100 | 90 | 100 | 100 | 100 | 20 | 100 |

| Cmpd. No. | 50 | 51 | 1A | 5A | 7A | 8A | 11A | 13A |
|---|---|---|---|---|---|---|---|---|
| Rate (kg/ha) | 0.1 | 0.1 | 0.1 | 0.1 | 0.1 | 0.1 | 0.1 | 0.1 |
| Species | | | | | | | | |
| Soybean | 90 | 100 | 40 | 10 | 20 | 10 | 10 | 70 |
| Wheat | 20 | 0 | 40 | 0 | 0 | 0 | 40 | 20 |
| Corn | 90 | 50 | 70 | 20 | 35 | 0 | 60 | 60 |
| Velvetleaf | 100 | 100 | 100 | 50 | 100 | 10 | 100 | 100 |
| Morningglory | 100 | 30 | 100 | 20 | 90 | 0 | 80 | 90 |
| Chickweed | 100 | ND | 100 | 0 | 95 | 0 | 100 | 100 |
| Cocklebur | 100 | 60 | 70 | 60 | 20 | 0 | 30 | 70 |
| Blackgrass | 60 | 70 | 35 | 0 | 20 | 10 | 60 | 40 |
| Green foxtail | 50 | 0 | 100 | 60 | 100 | 90 | 100 | 100 |
| Johnsongrass | 90 | 0 | 90 | 50 | 90 | 0 | 60 | 80 |

| Cmpd. No. | 17A | 20A | 22A | 23A | 25A | 27A | 29A |
|---|---|---|---|---|---|---|---|
| Rate (kg/ha) | 0.1 | 0.1 | 0.1 | 0.1 | 0.1 | 0.1 | 0.1 |
| Species | | | | | | | |
| Soybean | 0 | 90 | 0 | 0 | 10 | 0 | 0 |
| Wheat | 15 | 20 | 0 | 0 | 30 | 0 | 10 |
| Corn | 60 | 80 | 0 | 0 | 80 | 0 | 10 |
| Velvetleaf | 100 | 100 | 10 | 0 | 100 | 0 | 20 |
| Morningglory | 60 | 100 | 10 | 0 | 90 | 0 | 30 |
| Chickweed | 55 | 100 | 20 | ND | 100 | ND | ND |
| Cocklebur | 50 | 80 | 0 | 0 | 40 | 0 | 10 |
| Blackgrass | 20 | 40 | 0 | 0 | 50 | 0 | 0 |
| Green foxtail | 100 | 100 | 50 | 0 | 95 | 0 | 0 |
| Johnsongrass | 80 | 85 | 40 | 0 | 90 | 0 | 20 |

The designation ND signifies that there are no test data for that plant species at that rate of application.

TABLE 3
POSTEMERGENCE HERBICIDAL ACTIVITY (% CONTROL)

| Cmpd. No. | 1 | 2 | 3 | 4 | 5 | 6 | 7 | 8 |
|---|---|---|---|---|---|---|---|---|
| Rate (kg/ha) | 0.1 | 0.1 | 0.1 | 0.1 | 0.1 | 0.1 | 0.1 | 0.1 |
| Species | | | | | | | | |
| Soybean | 95 | 95 | 60 | 95 | 80 | 75 | 100 | 95 |
| Wheat | 40 | 30 | 30 | 80 | 30 | 30 | 70 | 70 |
| Corn | 60 | 80 | 40 | 95 | 70 | 70 | 100 | 80 |
| Velvetleaf | 100 | 100 | 100 | 100 | 95 | 95 | 100 | 100 |
| Morningglory | ND | 100 | 90 | ND | 60 | 60 | 100 | 100 |
| Chickweed | 100 | 100 | 100 | 100 | 40 | 10 | 100 | 100 |
| Cocklebur | 80 | 100 | 60 | 100 | 10 | 30 | 100 | 100 |
| Blackgrass | 30 | 20 | 20 | 95 | 20 | 30 | 100 | 95 |
| Green foxtail | 95 | 95 | 90 | 100 | 90 | 90 | 100 | 100 |
| Johnsongrass | 95 | 90 | 60 | 100 | 85 | 75 | 100 | 100 |

| Cmpd. No. | 9 | 10 | 11 | 12 | 13 | 14 | 20 | 21 |
|---|---|---|---|---|---|---|---|---|
| Rate (kg/ha) | 0.1 | 0.1 | 0.1 | 0.1 | 0.1 | 0.1 | 0.1 | 0.1 |
| Species | | | | | | | | |
| Soybean | 100 | 70 | 70 | 70 | 90 | 20 | 60 | 60 |
| Wheat | 85 | 40 | 40 | 50 | 80 | ND | 10 | 20 |
| Corn | 95 | 40 | 70 | 30 | 90 | 20 | 10 | 40 |
| Velvetleaf | 100 | 90 | 100 | 100 | 100 | 40 | 40 | 30 |
| Morningglory | 95 | 60 | 60 | 60 | 100 | 0 | 0 | 20 |
| Chickweed | 100 | 0 | 0 | 100 | 100 | 0 | 0 | 0 |
| Cocklebur | 100 | 40 | 20 | 30 | 100 | 0 | 0 | 0 |
| Blackgrass | 95 | 10 | 30 | 50 | 95 | 20 | 20 | 0 |
| Green foxtail | 100 | 80 | 90 | 100 | 100 | 0 | 50 | 80 |
| Johnsongrass | 100 | 80 | 70 | 80 | 100 | 0 | 20 | 60 |

| Cmpd. No. | 22 | 23 | 24 | 25 | 26 | 27 | 28 | 29 |
|---|---|---|---|---|---|---|---|---|
| Rate (kg/ha) | 0.1 | 0.1 | 0.1 | 0.1 | 0.1 | 0.1 | 0.1 | 0.1 |
| Species | | | | | | | | |
| Soybean | 80 | 95 | 90 | 70 | 100 | 95 | 30 | 30 |
| Wheat | 20 | 80 | 30 | 30 | 95 | 90 | 10 | 30 |
| Corn | 80 | 100 | 30 | 80 | 100 | 90 | 50 | 20 |
| Velvetleaf | 100 | 100 | 100 | 100 | 100 | 100 | 90 | 0 |
| Morningglory | 100 | ND | 70 | 60 | 100 | 100 | 30 | 0 |
| Chickweed | 0 | 100 | 30 | 20 | 100 | 100 | 40 | 20 |
| Cocklebur | 40 | 100 | 50 | 30 | 100 | 100 | 0 | 0 |
| Blackgrass | 0 | 95 | 20 | 30 | 100 | 95 | 40 | ND |
| Green foxtail | 95 | 100 | 60 | 85 | 100 | 100 | 0 | 0 |
| Johnsongrass | 70 | 100 | 85 | 80 | 100 | 95 | 20 | 0 |

| Cmpd. No. | 30 | 31 | 32 | 34 | 38 | 42 | 48 | 49 |
|---|---|---|---|---|---|---|---|---|
| Rate (kg/ha) | 0.1 | 0.1 | 0.1 | 0.1 | 0.1 | 0.1 | 0.1 | 0.1 |
| Species | | | | | | | | |
| Soybean | 95 | 95 | 95 | 100 | 100 | 70 | 10 | 100 |
| Wheat | 95 | 70 | 60 | 100 | 100 | 50 | 0 | 40 |
| Corn | 100 | 70 | 80 | 100 | 90 | 50 | 40 | 50 |
| Velvetleaf | 100 | 100 | 100 | 100 | 100 | 100 | ND | 100 |
| Morningglory | ND | 95 | 100 | 100 | 100 | 95 | 0 | 100 |
| Chickweed | 100 | 70 | 80 | 100 | 100 | 100 | 0 | 80 |
| Cocklebur | 100 | 85 | 60 | 100 | 100 | 50 | 0 | 100 |
| Blackgrass | 100 | 70 | 80 | 100 | 100 | 0 | 0 | 30 |
| Green foxtail | 100 | 100 | 90 | 100 | 100 | 40 | ND | 20 |
| Johnsongrass | 100 | 90 | 80 | 100 | 100 | 70 | 10 | 70 |

| Cmpd. No. | 50 | 51 | 1A | 2A | 7A | 8A | 11A | 13A |
|---|---|---|---|---|---|---|---|---|
| Rate (kg/ha) | 0.1 | 0.1 | 0.1 | 0.1 | 0.1 | 0.1 | 0.1 | 0.1 |
| Species | | | | | | | | |
| Soybean | 90 | 70 | 50 | 40 | 60 | 40 | 60 | 90 |
| Wheat | 0 | 10 | 15 | 0 | 10 | 0 | 30 | 0 |
| Corn | 80 | 30 | 60 | 20 | 50 | 40 | 60 | 70 |
| Velvetleaf | 100 | 95 | 95 | 70 | 100 | 30 | 100 | 100 |
| Morningglory | 90 | 0 | 0 | 95 | 60 | 10 | 90 | 100 |
| Chickweed | 60 | 10 | 80 | 0 | 40 | 0 | 100 | 90 |
| Cocklebur | 90 | 70 | 75 | 20 | 100 | 50 | 100 | 100 |
| Blackgrass | 0 | 0 | 0 | 0 | 10 | 0 | 10 | 0 |
| Green foxtail | 40 | 0 | 90 | 0 | 90 | 40 | 90 | 90 |
| Johnsongrass | 40 | 0 | 80 | 0 | 90 | 30 | 50 | 70 |

| Cmpd. No. | 17A | 20A | 22A | 23A | 25A | 27A | 29A |
|---|---|---|---|---|---|---|---|
| Rate (kg/ha) | 0.1 | 0.1 | 0.1 | 0.1 | 0.1 | 0.1 | 0.1 |
| Species | | | | | | | |
| Soybean | 70 | 85 | 20 | 0 | 50 | 10 | 30 |
| Wheat | 0 | 0 | 0 | 0 | 30 | 0 | 30 |
| Corn | 40 | 60 | 10 | 20 | 40 | 30 | 20 |
| Velvetleaf | 100 | 100 | ND | ND | 100 | 20 | 70 |
| Morningglory | ND | 100 | 30 | 0 | 100 | 0 | 100 |
| Chickweed | 20 | 70 | 60 | 0 | 100 | ND | 0 |
| Cocklebur | 70 | 100 | 20 | 70 | 90 | 0 | 100 |
| Blackgrass | 15 | 10 | 0 | ND | 20 | 0 | 10 |
| Green foxtail | 80 | 70 | 0 | 0 | 100 | ND | 60 |
| Johnsongrass | 80 | 50 | 0 | 0 | 70 | 0 | 10 |

The designation ND signifies that there are no test data for that plant species at that rate of application.

I claim:

1. A compound of the formula or

-continued

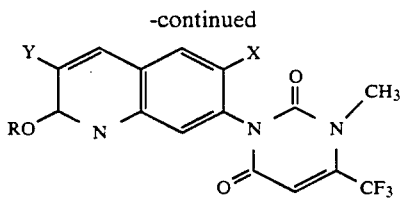

in which

R is lower alkyl, lower alkenyl, lower alkynyl, lower haloalkyl, lower cyanoalkyl, lower alkoxy, lower alkoxy lower alkylene, and benzyl;

X is hydrogen or halogen; and

Y is hydrogen, lower alkyl, lower haloalkyl, halogen, lower alkoxy, lower haloalkoxy, lower alkythio, lower alkoxy lower alkylene, lower alkylthio lower alkylene, and hydroxy.

2. A compound of claim 1 of the formula

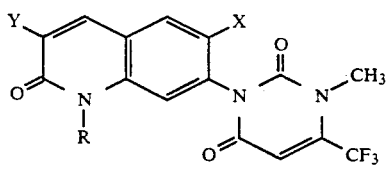

in which R is lower alkyl, lower alkenyl, lower alkynyl, lower haloalkyl, and lower cyanoalkyl; X is hydrogen or fluorine; and Y is hydrogen or lower alkyl.

3. A compound of claim 2 in which R is ethyl, propyl, allyl, or propargyl; X is hydrogen or fluorine; and Y is hydrogen or methyl.

4. A compound of claim 3 in which X is fluorine; and Y is hydrogen.

5. The compound of claim 4 in which R is ethyl.
6. The compound of claim 4 in which R is propyl.
7. The compound of claim 4 in which R is allyl.
8. The compound of claim 4 in which R is propargyl.
9. A compound of claim 3 in which X is fluorine; and Y is methyl.
10. The compound of claim 9 in which R is allyl.
11. The compound of claim 9 in which R is propargyl.
12. A compound of claim 1 of the formula

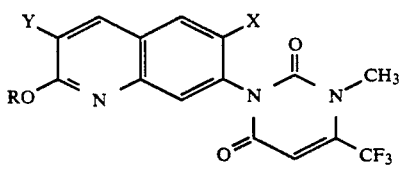

in which R is lower alkyl, lower alkenyl, lower alkynyl, lower haloalkyl, and lower cyanoalkyl; X is hydrogen or fluorine; and Y is hydrogen or lower alkyl.

13. A compound of claim 12 in which R is ethyl, propyl, allyl, or propargyl; X is hydrogen or fluorine; and Y is hydrogen or methyl.

14. A compound of claim 13 in which X is fluorine; and Y is hydrogen.

15. A compound of claim 13 in which X is fluorine; and Y is methyl.

16. A herbicidal composition comprising an herbicidally effective amount of a compound of claim 1 in admixture with an agriculturally acceptable carrier.

17. The method of controlling undesired plant growth which comprises applying to the locus where control is desired a herbicidally effective amount of a composition of claim 16.

* * * * *